US00PP11497P

United States Patent [19]

Boeder

[11] Patent Number: Plant 11,497

[45] Date of Patent: Sep. 5, 2000

[54] CHRYSANTHEMUM PLANT NAMED 'KINGFISH'

[75] Inventor: Mark Boeder, West Wittering, United Kingdom

[73] Assignee: Cleangro Limited, West Sussex, United Kingdom

[21] Appl. No.: 09/038,786

[22] Filed: Mar. 11, 1998

[51] Int. Cl.[7] ..... A01H 5/00

[52] U.S. Cl. ..... Plt./286

[58] Field of Search ..... Plt./286, 287, 295, Plt./296

[56] References Cited

U.S. PATENT DOCUMENTS

P.P. 1,548 1/1957 Boerner ..... Plt./293

OTHER PUBLICATIONS

UPOV–ROM, 1999/02, Plant Variety Database, GTI Jouve Retrieval Software, citation for 'Kingfisher'.

*Primary Examiner*—Howard J. Locker
*Attorney, Agent, or Firm*—Christie, Parker & Hale, LLP

[57] ABSTRACT

A new plant variety of Chrysanthemum producing orange/yellow bicolor flowers.

2 Drawing Sheets

BACKGROUND OF THE INVENTION

The present invention is directed to a new and distinct variety of Chrysanthemum botanically classified as *Dendranthema grandiflora*. The varietal denomination of the new chrysanthemum is 'Kingfish'.

The female parent of the new variety is the variety known as 'Jessica' (U.S. Plant Pat. No. 7,587) and the male parent is an undistributed, unnamed, seedling identified as 'G10-C3'. The new variety has been asexually reproduced by vegetative cuttings in Ventura County, Calif. and the distinguishing characteristics are retained through successive generations of asexual reproduction.

SUMMARY OF THE INVENTION

'Kingfish' is a pot type Chrysanthemum plant variety that produces orange/yellow bicolored flowers.

Comparison with 'Jessica'

'Kingfish' differs from 'Jessica' in flower color. The new variety produces orange/yellow bicolor flowers and 'Jessica' produces yellow flowers.

BRIEF DESCRIPTION OF ILLUSTRATIONS

The accompanying photographs show a typical specimen of potted plant of the new variety and of flowers of the new variety, with colors being as nearly true as possible with illustrations of this type.

DESCRIPTION OF THE PLANT

Figure 1:
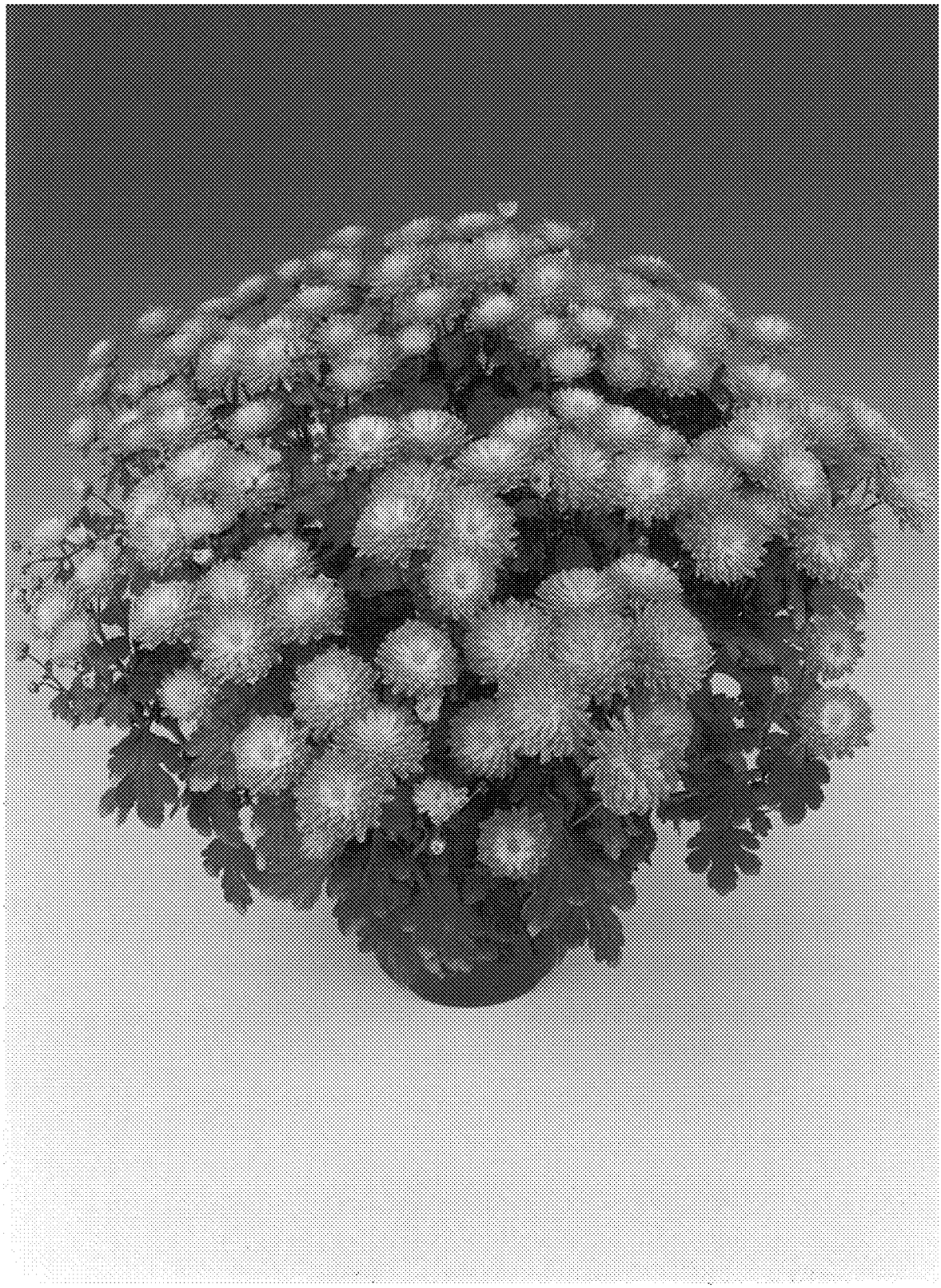
FIG. 1 is a whole plant view of the new cultivar grown in a pot.
Figure 2:
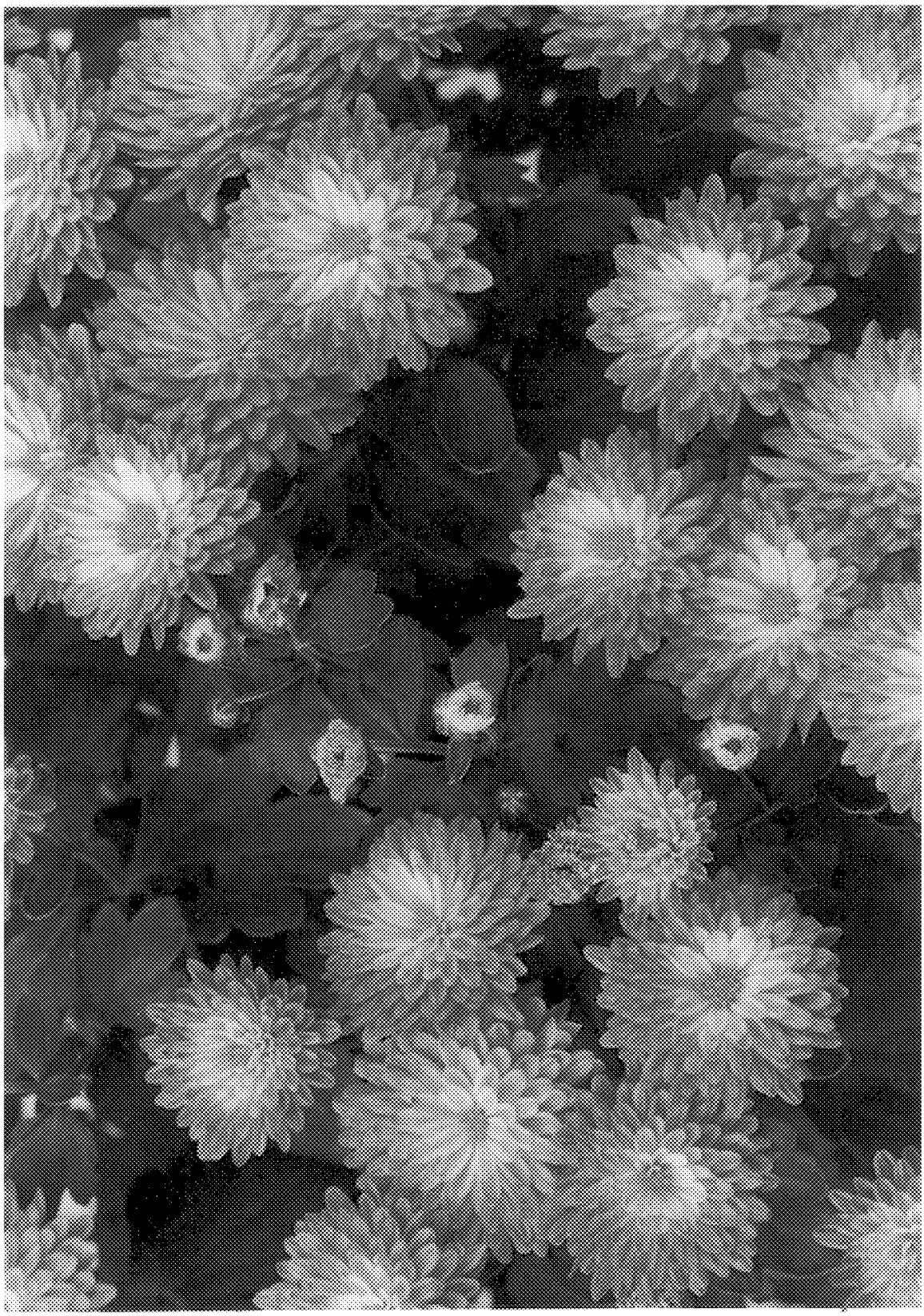
FIG. 2 is a closer view, showing inflorescence and foliage characteristics of the new cultivar in greater detail.

The following description of the new variety is of specimens grown in a greenhouse in Ventura County, Calif. in the month of October. 'Kingfish' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once ten days after planting which results in about 3 breaks per pinch. It has been observed that the shelf life of 'Kingfish' is about 22 days with the response time of about 7.5 weeks. No treatment with growth retardant is required. Useful growing conditions include night temperatures of about 64°–66° F., day temperatures of about 80°–85° F. and about 5,000 foot-candles of light.

Plant:
- *Habit.*—Upright.
- *Height.*—About 32 cm.
- *Number of breaks from pinch.*—About 3.
- *Typical container sizes commercially grown in.*—6 inch, 1 gallon, 3 gallon containers.
- *Length of lateral branches.*—About 26 cm.
- *Stem color.*—Near 146D.

Foliage:
- *Leaf arrangement.*—Alternate.
- *Number of leaves per lateral branch.*—About 15.
- *Leaf size. Length: About* 7.8 cm. Width: About 4.7 cm.
- *Leaf shape.*—Ovate.
- *Attachment.*—Petioled.
- *Leaf apex.*—Obtuse.
- *Base.*—Tapered.
- *Margin.*—Lobed, with some crenations.
- *Aspect.*—Flat.
- *Surface.*—. Top: Pubescent. Bottom: Pubescent.
- *Petiole length.*—About 1.8 cm. Color: Near 146D.
- *Mature leaf. Top: Near* 137A. Bottom: Near 137C.
- *Young leaf. Top: Near* 137A. Bottom: Near 137B.

Flower:
- *Inflorescence form.*—Cyme.
- *Flower form.*—Daisy during all stages of bloom maturity.
- *Number of blooms per branch.*—About 11.
- *Diameter of fully expanded bloom.*—About 5 cm.
- *Depth of fully expanded bloom.*—About 1.5 cm.
- *Sepal number.*—About 10.
- *Color.*—Near 137A.
- *Peduncle.*—Length: Lowermost peduncles about 13 cm, terminal peduncles about 3 to 4 cm. Habit: Straight. Surface: Slightly pubescent.
- *Flower bud shape.*—Sphere.
- *Diameter.*—About 0.6 cm.
- *Height.*—About 0.6 cm.
- *Ray florets.*—. Number per flower: About 130. Shape: Oblanceolate. Apex: Obtuse. Base: Tapered. Margin:

Entire. Aspect: Slightly incurved. Length: About 2.2 cm. Width: About 0.5 cm.

*Disc florets.*—Number per flower: About 15. Shape: Cylindric. Length: About 0.5 cm. Width: About 0.1 cm. Diameter of disc: About 1.4 cm.

*Fragrance.*—Strong, musky.

Flower color:

*General flower coloration.*—Red bronze with a yellow center.

*Ray florets, top side.*—Immature: Near 7D. Mature: Near 181 A top; near 9B base. Fading: Near 181B 6C base and streaks.

*Ray floret, under side.*—Immature: Near 8B. Mature: Near 8B with near 181B streaks. Fading: Near 11B.

*Disc florets.*—Mature: Near 15B.

*Changes as the flower ages.*—Center is completely yellow, bronze coloration becomes more prominent as outer ray florets fully open, flower form remains flat.

Reproductive organs:

*Ray florets.*—Pistillate. Stigma shape: 2 branched. Stigma color: Near 7A. Style length: About 0.5 cm.

*Disc florets.*—Stigma shape: 2 branched. Stigma color: Near 12A. Style Length: About 0.4 cm. Stamen number: About 5. Anther length: About 0.15 cm. Pollen color: Near 14A. Pollen quantity: Abundant.

What is claimed is:

1. A new and distinct Chrysanthemum plant of the variety substantially as herein shown and described.

* * * * *